(12) United States Patent
Arjmand et al.

(10) Patent No.: US 10,479,815 B2
(45) Date of Patent: Nov. 19, 2019

(54) PROTEIN PURIFICATION USING INTEIN-HYDROPHOBIN TAG AND ALCOHOL PRECIPITATION

(71) Applicants: Sareh Arjmand, Tehran (IR); Sahar Nejatipoor, Tehran (IR); Seyed Omid Ranaei Siadat, Tehran (IR)

(72) Inventors: Sareh Arjmand, Tehran (IR); Sahar Nejatipoor, Tehran (IR); Seyed Omid Ranaei Siadat, Tehran (IR)

( * ) Notice: Subject to any disclaimer, the term of this patent is extended or adjusted under 35 U.S.C. 154(b) by 0 days.

(21) Appl. No.: 16/055,041

(22) Filed: Aug. 4, 2018

(65) Prior Publication Data

US 2018/0371011 A1    Dec. 27, 2018

(51) Int. Cl.
*C07K 1/30* (2006.01)
*C12N 15/81* (2006.01)
*C07K 16/22* (2006.01)
*C07K 1/02* (2006.01)

(52) U.S. Cl.
CPC .............. *C07K 1/30* (2013.01); *C07K 16/22* (2013.01); *C12N 15/815* (2013.01); *C07K 2319/01* (2013.01); *C07K 2319/92* (2013.01)

(58) Field of Classification Search
None
See application file for complete search history.

(56) References Cited

U.S. PATENT DOCUMENTS

2006/0141570 A1    6/2006  Wood
2015/0057434 A1    2/2015  Schelle
2015/0353597 A1   10/2015  Chen

OTHER PUBLICATIONS

Kirkland et al. (J Ind Microbiol Biotechnol (2011) 38:327-335).*
Mills et al. (The Journal of Biological Chemistry vol. 289, No. 21, pp. 14498-14505, May 23, 2014).*
Du J and Rehm BHA, "Purification of target proteins from intracellular inclusions mediated by intein cleavable . . . ", Microb Cell Fact, 16:2553-2560, (2017).
Guan D, et al., "Split intein mediated ultra-rapid purification of tagless protein (SIRP)", Biotechnol Bioeng, 110:2471-2481, (2013).
Linder MB, et al., "Efficient purification of recombinant proteins using hydrophobins as tags in surfactant-based two-phase systems", Biochem, 43:11873-11882, (2004).

* cited by examiner

*Primary Examiner* — Suzanne M Noakes
*Assistant Examiner* — Jae W Lee
(74) *Attorney, Agent, or Firm* — Mehran Kasra

(57) ABSTRACT

A method of downstream purification of a recombinant protein in fusion with a hydrophobin-intein tag using alcohol precipitation. The method comprises (1) constructing a plasmid expressing a fusion protein in a host cell, wherein the fusion protein includes a target protein domain, an intein, and a hydrophobin domain; (2) culturing the host cell transfected with the plasmid forming a cell culture medium; (3) separating a cell culture supernatant containing the fusion protein from the cell culture medium; and (4) purifying a substantial amount of the target protein from the cell culture supernatant without its hydrophobin-intein fusion tag using alcohol precipitation.

14 Claims, 6 Drawing Sheets

Specification includes a Sequence Listing.

PROTEIN PURIFICATION USING INTEIN-HYDROPHOBIN TAG AND ALCOHOL PRECIPITATION

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING SUBMITTED ELECTRONICALLY

A sequence listing having the file name "Arjmand_SL_ST25.txt" created by Patent-in 3.5.1; on Jul. 27, 2018; and having a size of 16 kilobytes is filed in computer readable form concurrently with the specification. The sequence listing is part of the specification and herein incorporated by reference in its entirely.

BACKGROUND

Field of the Invention

The present invention relates to a method for purification and/or recovery of recombinant proteins expressed in recombinant cells. The recombinant proteins include any pharmaceutical and industrial useful proteins and are expressed as fusion with a hyrophobin-intein tag. In particular, the invention relates to a method for recovery of the intact recombinant protein from the hydrophobin-intein tag and other medium components using alcohol precipitation.

Description of the Prior Art

Advances in different protein expression systems ensure the recombinant production of almost every protein of interest. However, these products, especially those with pharmaceutical applications, require multiple costly subsequent purification steps and each step can inevitably decrease the final yield of the product. A protein purification process could accounts for up to 80% of production cost in the manufacturing of recombinant protein which require significant downstream processing (Walsh, 2014). Therefore, optimization of recombinant protein purification processes for reliable, simple, and cost-effective strategies with the least number of steps is one of the main issues in the industrial biotechnology and bio-separation technology development.

Fusion of affinity tags to the target protein is a commonly used method to aid protein purification as well as improving protein expression, stability, and solubility. A wide range of fusion tags with different sizes and characteristics are available; for example, E. coli maltose-binding protein tag (MBP), the Schistosoma glutathione S-transferase tag (GST), and the polyhistidine tag (Terpe, 2003). The presence of affinity tags may interfere with the structure and/or activity of the target protein; or in some cases, like for clinical applications, is unwanted. Therefore, they are usually desired to be removed from the final product in a way to produce native proteins without any extraneous sequences. At present, different approaches are available for tag removal that involves using expensive proteases or hazardous chemicals. These processes are usually non-specific and inefficient, imposing further steps of chromatography for protein purification, which increase the cost and decrease the yield of protein products.

Based on a recently discovered self-splicing protein element known as intein, the need for proteolytic processing of the fusion protein can be avoided and the tag would be removed from the target protein in a controlled manner (Wood and Camarero, 2014).

An intein is a naturally occurring segment of a protein that is involved in protein splicing. Protein splicing is a post-translational process in which an internal segment of the protein, named intein, catalyzes its excision from a protein precursor and ligation of flanking regions, named exteins, resulting in production of two proteins (Wood and Camarero, 2014; Guan et al., 2013). Sequence alignment of inteins reveals that most inteins contain a cysteine (Cys), Threonine (Thr), or serine (Ser) residue at the N-terminus; and an asparagine (Asn) or glutamin (Gln) at the C-terminus, with histidine (His) as the penultimate residue. These residues are necessary in the splicing mechanism and act as nucleophiles to create an N—S or N—O acyl rearrangement depending on the residue. This forms a linear thioester or ester intermediate. It has been reported that the cleavage of Ssp DnaB mini-intein is affected by the amino acid directly adjacent to the C-terminal of the intein. Usually Cysteine (Cys), Serine (Ser), or Threonine (Thr) directly follow the intein C-terminus as the first residue of the C-extein (+1), with Cys being the most prevalent. The side chains of these residues attack the ester bond formed in the previous step resulting in transesterification. Intein excised following the peptide bond cleavage, coupled to succinimide formation at the conserved Asn/Gln residue in downstream splice junction. Spontaneous O—N acyl rearrangement leads to formation of peptide bond between two exteins. Wood et al. (2000) indicated that presence of Cys/Thr/Ser residues at the +1 position is not necessary for C-terminal cleavage, but their occurrence is able to modulate the cleavage rate. Therefore, for C-terminal cleavage, mutation of the first residue of the C-extein is not constrained.

Structural analysis suggests that inteins are generally composed of an endonuclease protein domain and a self-splicing mini-intein domain. The endonuclease domain is not necessary for splicing. Indeed, the endonuclease domain can be deleted to form a functional splicing mini-intein. For example, by deletion of the entire endonuclease domain from the *Mycobacterium tuberculosis* recA intein gene, this intein was reduced form a 440 amino acid protein to a functional mini-intein with 168 amino acids (Shemella et al., 2007; Shah and Muir, 2014).

Self-cleaving affinity tags are a special group of fusion tags that possess inducible proteolytic activity combined with an appropriate affinity. They enable target protein purification and separation to be achieved in a few steps, saving time and cost. The development of pH and temperature-controllable splicing inteins has further improved the simplicity and economic advantages of this technology. One example for pH and temperature-inducible splicing inteins is Ssp DnaB mini-intein. The DnaB gene, encoding for DNA helicase of the *cyanobactrium synechocystis* sp. Stain PCC 6830 (Ssp), contains an intein of 429 amino acid residues. Deletion of the central 275 amino acid residues resulted in a splicing-proficient of minimal intein (Ssp DnaB mini-intein) consisting of the N-terminal 106 residues and the C-terminal 48 residues (Topilina and Mills, 2014).

Intein function can be modified from splicing to cleavage by replacing the conserved residue at C or N-terminal. For example, replacing N-terminal Cys with Ala abolishes the N-terminal cleavage and eliminates the splicing. In this case the C-terminal cleavage is observed. On the other hand, replacing the Asn in the C-terminal with Ala results in N-terminal cleavage. Blocking the splicing steps allowed the development of self-cleaving affinity tags (Shah and Muir, 2014).

The use of intein-mediated purification of proteins have been disclosed in different patent applications. Intein-mediated protein purification, using in vivo expression of an aggregator protein, was reported in patent application publication U.S. Pat. Appl. Pub. No. US 20060141570 A1; wherein the aggregator protein could be one or more phasins that was capable of specific association with granules of polyhydroxyalkanoate (PHA). The aggregator protein formed a complex with an insoluble PHA granule with low solubility using a solvent (non-alcohol) and separated from the cell lysate by centrifugation. The purification of the mentioned invention was followed by an additional downstream purification step for separation of intein-aggregator tag from the target protein in which cleavage could be controlled by pH, temperature, salt concentration, or free sulfhydryl concentration.

Tag removal remains an expensive and challenging issue in protein purification when an intact protein is needed. Inteins are used for controllable tag removal by inducing auto-cleavage as a separate step at the end of purification process. Cleavage is induced by providing preferred cleavage conditions, such as reducing agent, pH, and temperature, wherein the tag is separated from the target protein.

Du et al. (2007) demonstrated that by using an intein cleavable polyhydroxyalkanoate (PHA) synthase fusion, recombinant proteins can be first produced and sequestered on a natural resin. The polyhydroxyalkanoate inclusions were then separated from contaminating host proteins via simple PHA bead isolation steps. Finally the host proteins were purified by specific release into the soluble fraction induced by a pH reduction.

Chen et al., in patent application publication U.S. Pat. Appl. Pub. No. 20150353597 A1, used a method for purifying a protein of interest fused to the C-terminus of an intein C-fragment with a fusion protein comprising an intein N-fragment and a purification tag. The fusion protein first purified from other proteins, and the cleavage of protein of interest from intein C-fragment was then induced to release the protein of interest. In this case, separation of purification tag and intein C-fragment form the protein of interest was done in another step of purification.

Previous intein-mediated purification methods disclosed in different patent applications, can still benefit from reducing the number of purification steps and expensive protein separation using affinity columns.

Hydrophobins are a group of small surface-active proteins produced by filamentous fungi. Hydrophobins are relatively small (approximately 100 amino acids), contain eight disulfide-forming Cys residues in a conserved pattern, and could self-assemble on interfaces. Using hydrophobin as self-assembly tags are applicable and has many advantages such as considerable selectivity, high yield, and being simple to perform hydrophobin aggregation technically (Linder et al., 2004).

Hydrophobins which are identified to date are generally classified as either class I or class II. Both types have been identified in fungi as secreted proteins that self-assemble at interfaces into amphipathic films. Assemblages of class I hydrophobins are generally relatively insoluble whereas those of class II hydrophobins readily dissolve in a variety of solvents. The hydrophobins of interest to us are the class II from *Trichoderma reesei*. The hydrophobins number I and II (HFBI and HFBII) of *Trichoderma reesei* have been most extensively studied. Both have a size of about 7.5 KDa and are widely used in molecular studies (Joensuu et al., 2010; Linder et al., 2001).

Alcohol precipitation has been used in different purification methods including purification of hydrophobin as the target protein as described in patent application publication No, 20150057434 A1. However, alcohol precipitation has not been used for purification of other proteins when the hydrophobin is used as the fusion tag in combination with intein (intein-hydrophobin tag) to purify an intact protein.

SUMMARY OF THE INVENTION

It is the object of the present invention to provide a protein purification system which can operate rapidly, efficiently, and cheaply; for example, avoiding using expensive materials such as affinity columns and proteases as well as reducing the number of purification steps; thereby, overcoming the disadvantages of currently employed protein purification systems, such as involving too many steps, complicated manipulation, and high expenses.

The invention is directed to a method of purifying a target protein from a cell culture supernatant. The cell culture supernatant includes a recombinant fusion protein comprising a target protein domain, a self-cleaving intein, and a hydrophobin protein domain. The intein is located between the target protein domain and the hydrophobin protein domain. The hydrophobin protein domain is optionally linked by an amino acid linker to a self-cleaving intein. The method of producing the cell culture supernatant comprises nucleic acids encoding the recombinant fusion protein, constructing plasmids carrying the nucleic acids, cells stably transfected with the plasmids, and culturing the cells.

In a preferred embodiment, the invention is directed to a method of purifying a target protein from a cell culture supernatant comprising:
(a) preparing a cell culture supernatant, wherein the cell culture supernatant comprising a recombinant fusion protein, and wherein the recombinant fusion protein comprising a target protein domain, a self-cleaving intein, and a hydrophobin protein domain;
(b) adding a C1-C3 alcohol to the cell culture supernatant making a first alcohol solution;
(c) stirring the first alcohol solution forming a first stirred solution;
(d) centrifuging the first stirred solution forming a first precipitate and a first supernatant solution, wherein the first supernatant solution comprises the fusion protein;
(e) separating the first supernatant solution comprising the fusion protein;
(f) adding a C1-C3 alcohol to the first supernatant solution making the second alcohol solution;
(g) stirring the second alcohol solution forming a second stirred solution;
(h) centrifuging the second stirred solution forming a second precipitate comprising the product protein; and
(i) separating the second precipitate comprising the target protein to yield a substantial amount of the purified target protein.

The system and method of the invention provide many advantages and new features including the following:

(1) Hydrophobin as the purification tag is used in combination with intein for purification of intact proteins.

(2) Alcohol precipitation is used for protein purification using hydrophobin as a fusion tag.

(3) There is no need for an extra step of fusion tag cleavage and separation, and it happens spontaneously after centrifuging the second stirred solution in step (h) above, therefore, reducing the number of purification steps.

BRIEF DESCRIPTION OF THE FIGURES

A fuller understanding of the nature and objects of the present invention will become apparent upon consideration of the following detailed description taken in connection with the accompanying drawings, wherein.

DETAILED DESCRIPTION OF THE PREFERRED EMBODIMENTS

Figure 1:
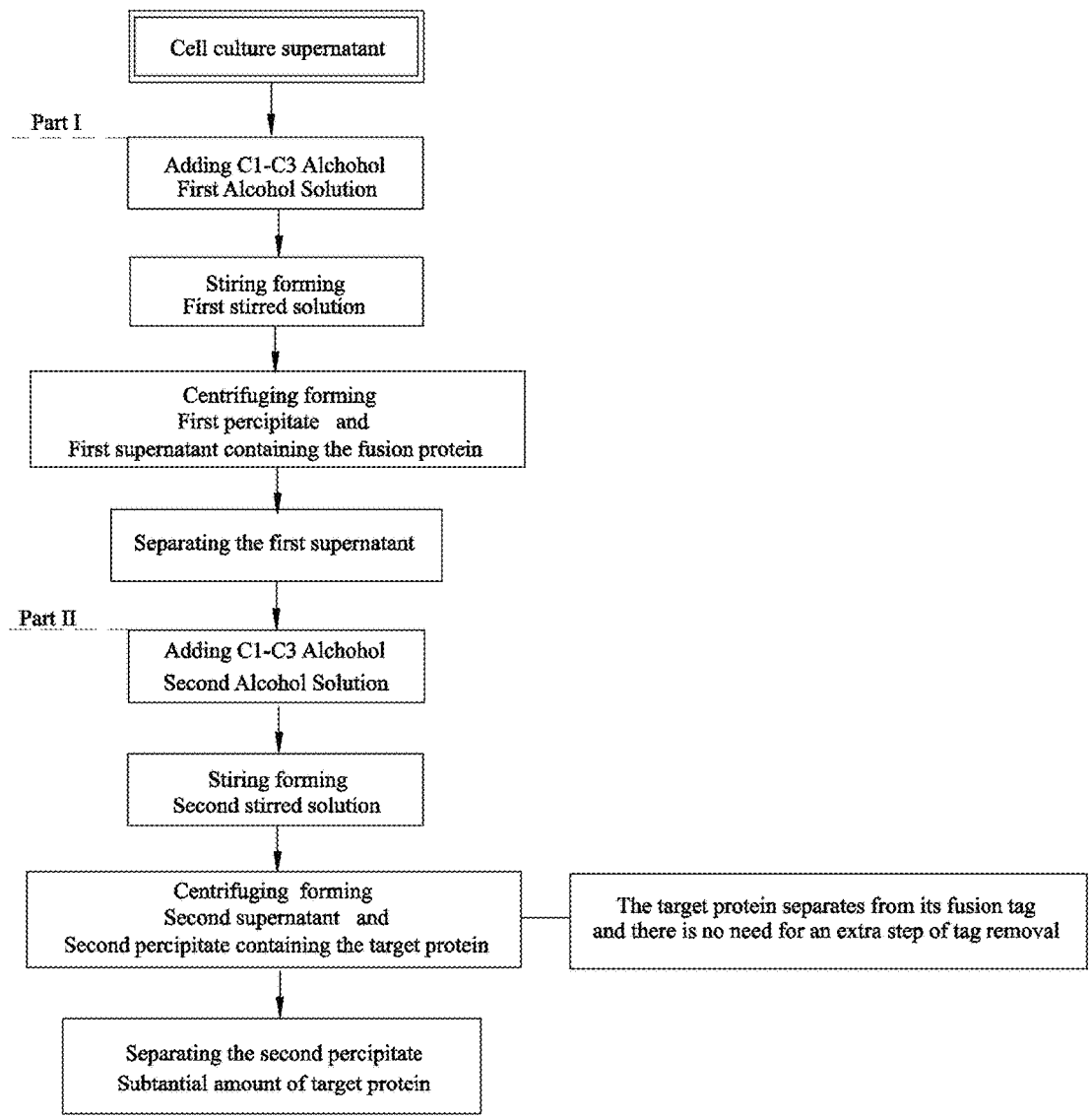
FIG. 1 shows a flow chart of a general protocol for purification of a target protein.

Unless defined otherwise, all technical and scientific terms used herein have the same meaning as commonly understood by one of ordinary skill in the art and as described in the literature, including books in cell biology, chemistry, and molecular biology (For example: Walsh, 2014; Terpe, 2003; and Wood and Camarero, 2014).

As used herein, the term C1-C3 alcohol refers to an alcohol selected from a group consisting of C1, C2, and C3 alcohols, preferably Methanol (C1), Ethanol (C2), and Propanol (C3). The volume fraction of an alcohol added to a solution, expressed as percentage, is the ratio of the volume of the alcohol divided by the sum of the volumes of the alcohol plus the volume of the solution the alcohol to be added measured separately. For example, to make a 50% v/v ethanol solution, you would measure 50 ml of ethanol and separately measure 50 ml of a solution, then mix the two together.

The terms recombinant fusion protein and fusion protein are used interchangeably and may also be sometimes referred to as hydrophobin-intein-target protein, preferably HFBII-intein-target protein. The terms recombinant target protein and target protein are used interchangeably. The term "cell culture supernatant" is used to address the solution containing the fusion protein at the start of the purification process and other supernatants obtained during the purification process are addressed by other terms such as first supernatants, second supernatants, etc.

In this invention we describe (1) a preparation process of a cell culture supernatant containing a recombinant fusion protein; and (2) a purification process of the recombinant target protein from the cell culture supernatant containing said recombinant fusion protein. These processes are illustrated in examples 1 to 5 in the section of examples.

The recombinant fusion protein comprises a target protein domain, a self-cleaving intein, and at least one hydrophobin protein domain. The intein is located between the target protein domain and the hydrophobin domain. Optionally, the hydrophobin domain could covalently be attached to the intein by an amino acid linker. The hydrophobin is hydrophbin I (HFBI) or hydrophobin II (HFBII), preferably hydrophobin II from *Trichoderma reesei*. The intein is preferably Ssp DnaB mini-intein from *Synechocystis* Sp. Pcc 6803. The target protein can be any recombinant protein from animals, plants, yeasts, or bacteria, for example, human vascular endothelial growth factor A 165 (VEGFA$_{165}$) or human alpha 1-antitrypsin (A1AT).

(1) Preparation of the cell culture supernatant: The cell culture supernatant is prepared by introducing an expression vector comprising a nucleic acid encoding said fusion protein into a host cell followed by culturing said host cell, illustrated in examples 1 to 5. The host cell may be derived from prokaryotes or eukaryotes, preferably a yeast cell of a strain from *Pichia pastoris*.

The vector is prepared by constructing an expression plasmid, preferably plasmid pPICZA (Example 1); amplifying it in a cell, preferably in *E. coli* (Example 2). The host cell, preferably *Pichia pastoris*, transfected with the plasmid is cultured forming a recombinant cell culture medium (Example 3), wherein the fusion protein is expressed in a plurality of the host cells (Example 4). The fusion protein is allowed to leave the host cells either by cell secretion or cell lysis into the recombinant cell culture medium. The cell culture supernatant is formed preferably by centrifuging the recombinant cell culture medium, and it is then separated, preferably by decanting. The cell culture supernatant containing the fusion protein is then used in the purification process of the target protein.

(2) Purification process: FIG. 1 shows a general scheme for purification of a target protein. The purification process comprises two parts, Part I and Part II. Each part comprises the steps of: an alcohol addition, a stirring, a centrifugation, a precipitation, and a separation as described below and illustrated in example 5.

Part I comprises adding a C1-C3 alcohol, preferably from about 50% (v/v) to about 75% (v/v), more preferably 66.66% (v/v) to 71.5% (v/v) of C2 alcohol, to the cell culture supernatant, making a first alcohol solution; stirring the first alcohol solution, preferably for 15-45 min and preferably at room temperature, forming a first stirred solution; centrifuging the first stirred solution, preferably for 30-45 min at 1300-1500 g, forming a first precipitate containing the cell residue and a first supernatant solution comprising a substantial amount of the fusion protein. The first supernatant solution is decanted and separated.

Part II comprises adding a C1-C3 alcohol, preferably about 50% (v/v) to about 66.66% (v/v) of C2 alcohol, and more preferably 54.54% (v/v) of C2 alcohol, to the first supernatant solution from Part I making the second alcohol solution; stirring the second alcohol solution, preferably for 15-45 min, preferably at room temperature, forming a second stirred solution; centrifuging the second stirred solution, preferably for 30-45 min at 1300-1500 g, wherein the target protein separates from the fusion protein and precipitates, forming a second precipitate containing the target protein and a second supernatant. The second supernatant is decanted and the second precipitate containing the target protein is then separated to yield a substantial amount of the purified target protein.

One of the advantages of the purification procedure described in this invention is that there is no need for an extra step of fusion tag cleavage and separation, while this happens spontaneously in the second alcohol purification step described in Part II.

The present invention will be illustrated in more details with reference to the following examples. Examples 1 to 5 describes an embodiment related expression and purification of VEGFA$_{165}$ as a target protein. The processes described in examples 1 to 5 are then repeated in another embodiment related to expression and purification of A1AT as a target protein. These examples are presented only for illustrative purpose and are not intended to limit the scope of the present invention in any way.

VEGFA$_{165}$ from human (SEQ ID No: 4) as a target protein

Example 1

Construction of Expression Plasmid pPICZA for Expression of the Fusion Protein Hydrophobin-Intein-VEGF A$_{165}$ For constructing hydrophobin-intein-VEGFA$_{165}$; the sequences of protein HFBII from *Trichoderma reesei* with its native signal peptide (SEQ ID No: 1); Ssp Dnab mini-intein from *Synechocystis* Sp. Pcc 6803 with an optional additional Cystein amino acid at the C-terminal for improving splicing (SEQ ID No: 2); an optional linker with 12 amino acids at the N-terminal (SEQ ID No: 3); and VEGFA$_{165}$ from human (SEQ ID No: 4) were converted to the nucleotide sequence according to the codon bias of yeast *Pichia pastoris*. The sequence with restriction site for EcoRI/KpnI restriction enzyme at the 5' and 3' end and kozak sequence of AOX1 gene from *Pichia pastoris*, after EcoRI restriction recognition site and just before beginning ATG, was chemically synthesized (SEQ ID No: 5).

Figure 2:
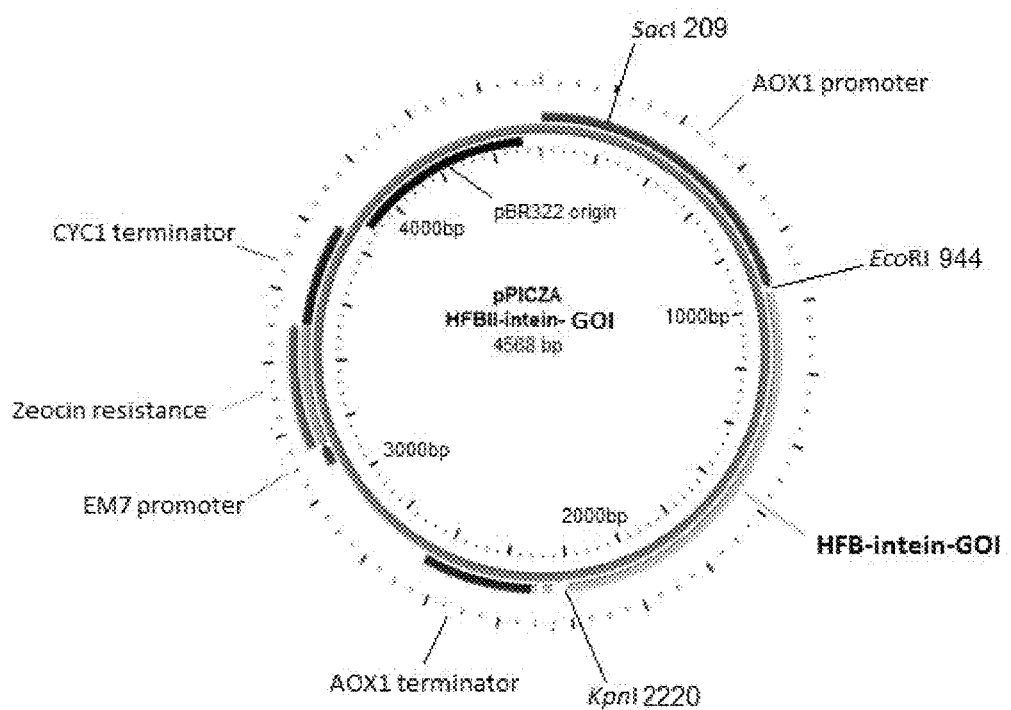
FIG. 2 is a schematic shape showing recombinant plasmid pPICZA containing HFBII-intein-Gene Of Interest (GOI) sequence between EcoRI/KpnI restriction sites.

The synthetic sequence was cloned between EcoRI and KpnI restriction site behind the AOX1 promoter in the pPICZA plasmid (FIG. 2).

Example 2

Transformation of HFBII-Intein-VEGFA$_{165}$ in *E. coli* (Strain DH5α)

pPICZA vector carrying expression construct for HFBII-intein-VEGFA$_{165}$ chimeric gene was transformed to *E. coli* (strain DH5α) and recombinant clones were selected. The transformants were plated on low salt LB agar plates containing Zeocin® (25 µg/ml) for selection. The positive clones were inoculated in 5 ml low salt medium supplemented with Zeocin® (25 µg/ml) and incubated over night at 37° C. The amplified recombinant plasmid pPICZA containing DNA sequence of HFBII-intein-VEGFA$_{165}$ construct was extracted from the bacteria and sent for sequencing to confirm the proper sequences.

Example 3

Transformation of *Pichia pastoris* and Selection of *Pichia pastoris* Transformants Recombinant vector pPICZA, containing DNA sequence of HFBII-intein-VEGFA$_{165}$ construct, was linearized with SacI in the AOX1 promoter region to stimulate homologous recombination when the plasmid is transformed into the *Pichia pastoris* competent cells. Linearized DNA were integrated into AOX1 promoter region of *Pichia pastoris* to give the desired strain. To make competent cells, *Pichia pastoris* (X33) was cultured overnight in 50 mL of YPD medium at 30° C. 500 mL of YPD medium was inoculated with 0.1-0.5 mL of the cultured medium in a 2 L flask and incubated at 30° C. to reach an OD$_{600}$ of 1.3-1.5. After centrifugation at 1500 g at 4° C. for 5 min, the pellet was dissolved in 500 mL of cold sterilized deionized water. After re-centrifugation under the same conditions, the pellet was dissolved in 250 mL of cold sterilized water. The same procedure was repeated with 20 mL and then 1 mL of cold 1 M sorbitol to give competent cells at a final volume of 1 mL. 80 µL of the competent cell was mixed with 1-5 µg of recombinant vector pPICZA linearized with SacI and incubated in an electroporation cuvette for 5 min on ice. The competent cells electroporated at 1500 volt, 200Ω and 25 UF and immediately were re-suspended in 1 ml of 1 M sorbitol and transferred to sterilized microcentrifuge tubes. The transformant were plated in YPD agar supplemented with Zeocin® (100 µl/ml) and grown for 3 days at 30° C.

The genomic DNAs of transformant were extracted and analyzed for the correct integration of HFBII-intein-VEGFA$_{165}$ construct in yeast chromosome using PCR with the 5' AOX1 primer (5'-GACTGGTTCCAATTGACAAGC-3') and 3' AOX1 primer (5'-GCAAATGGCATTCT-GACATCC-3) and sequencing of PCR results.

Figure 3:
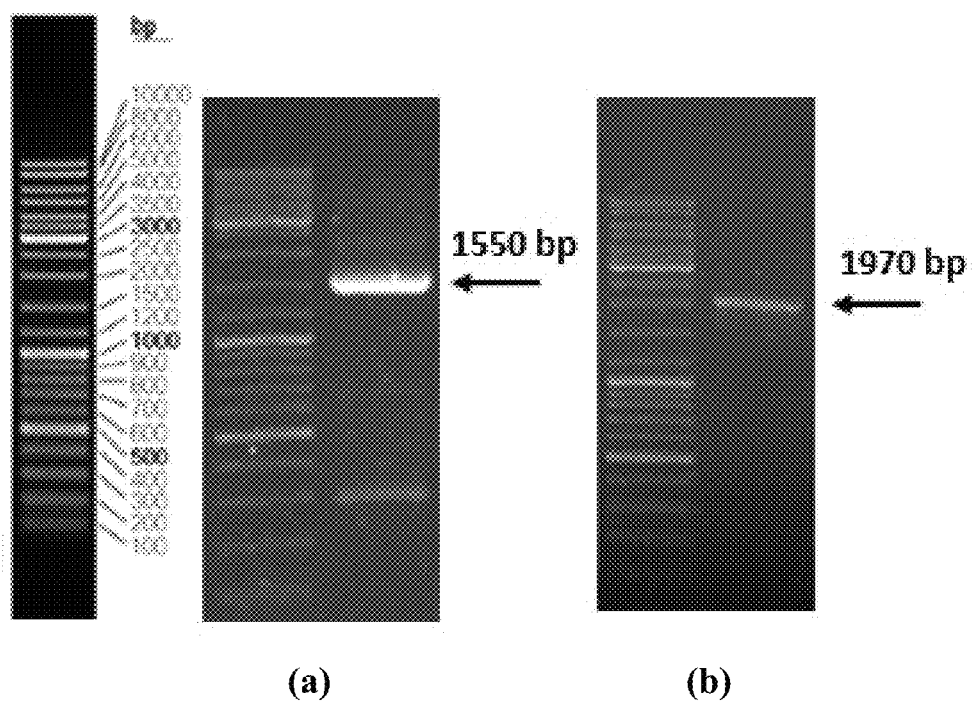
FIG. 3 is an agarose gel electrophoresis showing PCR amplification of (a) HFBII-intein-VEGFA$_{165}$ and (b) HFBII-intein-A1AT constructs with AOX1 primers. The related 1.5 kb and 2 kb PCR bands were observed in agarose gel electrophoresis.

DNAs amplified by the PCR were found to be about 1.5 Kb in size, as indicated by agarose gel electerophoresis (FIG. 3a).

Example 4

Expression of Recombinant Chimeric Protein HFBII-Intein-VEGFA$_{165}$

Colonies of transformant *Pichia pastoris* carrying HFBII-intein-VEGFA$_{165}$ sequence were used for inoculation of 25 ml of YPG in a 250 ml flask and grown at 28-30° C. in a shaking incubator (250-300 rpm) until culture reached an OD$_{600}$ of 2-6 (approximately 16-18 hours). The cells were harvested by centrifuging at 1500 g for 5 min and resuspended in YPM (containing 0.5% methanol to induce the expression and pH was set at 7.8) to reach an $OD_{600}$ of 1. Methanol was added to the culture every 24 hours for 96 hours to maintain induction (1% at the first day and 0.5% in the next days of induction). The culture was then centrifuged at 3000 g for 5-10 min, and the supernatant was transferred to a separate tube for analysis of protein expression by silver nitrate stained SDS-PAGE and ELISA.

ELISA was conducted to measure the quantities of the expressed chimeric protein HFBII-intein-$VEGFA_{165}$ using human VEGF DueSet ELISA kit (R & D systems, DY293B-05) according to the manufacturer's protocol. The ELISA experiment detected the recombinant secretory $VEGFA_{165}$ with concentration of 53 mg/mL in the culture supernatant.

Figure 4:
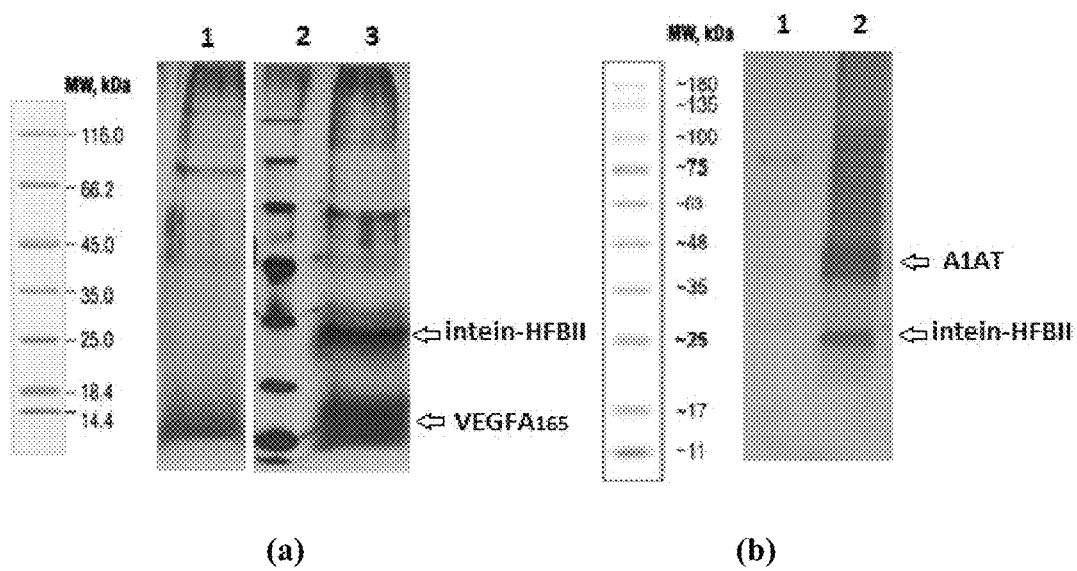
FIG. 4 is a SDS-PAGE showing the expression of recombinant (a) HFBII-intein-VEGFA$_{165}$ and (b) HFBII-intein-A1AT. Lane 1a) control negative containing the supernatant of non-recombinant *Pichia pastoris*. Lane 2a) protein marker. Lane 3a) the supernatant of recombinant *Pichia pastoris* expressing HFBII-intein-VEGFA$_{165}$. Lane 1b) protein marker. Lane 2b) the supernatant of recombinant *Pichia pastoris* expressing HFBII-intein-A1AT. The cleaved HFBII-intein is observed in ~33 kD. The recombinant VEGFA$_{165}$ and A1AT is observed in ~23 and ~50 kD respectively. The intein cleavage was triggered during the SDS-PAGE preparation and loading.

To observe the secretory expressed protein, 10 μL of supernatant were subjected to 12% SDS-PAGE. The proteins were visualized as bands by staining with silver nitrate to determine whether the recombinant chimeric protein were expressed and secreted (FIG. 4).

Example 5

Purification of $VEGFA_{165}$ as a Target Protein (FIG. 1)

Figure 5:
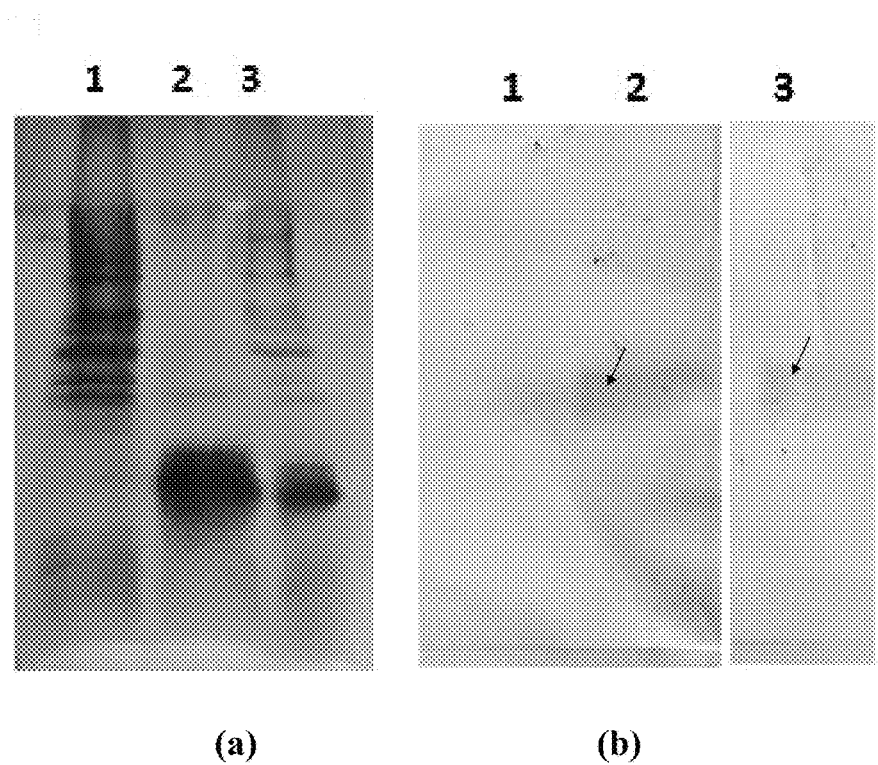
FIG. 5 Purification of VEGFA$_{165}$ and western blot of purified protein. Lane 1a) the first precipitation of purification, containing all protein of media except target protein. Lane 2a) the second precipitation of purification, containing the purified target protein (VEGFA$_{165}$). Lane 3a) supernatant of recombinant yeast cell culture expressing VEGFA$_{165}$ without HFBII-intein fusion partner as the positive control. Lane 1b) western blot of the first precipitation of purification, containing all protein of media except target protein. Lane 2b) western blot of the second precipitation of purification, containing the purified target protein (VEGFA$_{165}$). Lane 3b) supernatant of recombinant yeast cell culture expressing VEGFA$_{165}$ without HFBII-intein fusion partner as the positive control.

To purify recombinant $VEGFA_{165}$ (fused with HFBII using intein) from the supernatant of the yeast culture medium (cell culture supernatant), 50% (v/v) to 75% (v/v) of C1-C3 alcohol was added to the cell culture supernatant (first alcohol solution), while 66.66% (v/v) of C2 alcohol was preferable. The solution was stirred at room temperature for 30 min (first stirred solution). The mixture (first stirred solution) was centrifuged for 30-45 min at 14000 g (first centrifugation) and the supernatant containing the fusion protein (first supernatant) was decanted into a clean vials. From 50% (v/v) to 66.66% (v/v) of C1-C3 alcohol was added to the first supernatant (second alcohol solution), while 54.54% (v/v) of C2 alcohol preferable. The solution was stirred for 30 minutes at room temperature (second stirred solution) and centrifuged for 30-45 minutes at 14000 g (second centrifugation). The condition of experiment in second stirring and centrifugation appeared to induce the autolytic property of used intein and the $VEGFA_{165}$ was separated from the rest of construct and precipitated. The hydrophobin and fused intein stayed in the alcohol solution and separated from the precipitate. The obtained precipitate consisted of the target protein ($VEGFA_{165}$) was dissolved in water and subjected to the SDS-PAGE to be visualized. The results of SDS-PAGE indicated that the $VEGFA_{165}$ was separated from the other components with a high purity (FIG. 5). The results of ELISA experiments verified the presence of recombinant $VEGFA_{165}$ in the dissolved solution of second precipitate and its absence in the solution of first precipitate.

Human A1AT (SEQ ID No: 6) as a target protein

The expression and purification processes for A1AT protein were performed by repeating the examples 1 to 5 while substituting $VEGFA_{165}$ protein with A1AT protein, including:

(i) Construction of expression plasmid pPICZA for expression of the fusion protein hydrophobin-intein-A1AT, similar to Example 1, but including the sequences of HFBII (SEQ ID No: 1), intein (SEQ ID No: 2), optional linker (SEQ ID No: 3), and A1AT protein (SEQ ID No: 6) which was converted to the nucleotide sequence, based on the codon preference of *Pichia pastoris*, and chemically synthesized for the hydrophobin-intein-linker-A1AT (SEQ ID No: 7).

Figure 6:
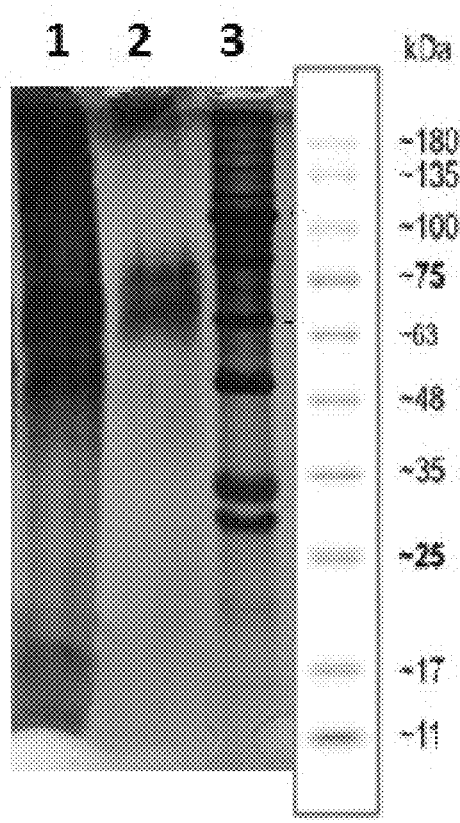
FIG. 6 is a SDS-PAGE showing purified A1AT. Lane 1) supernatant of transformant yeast cell culture before purification. Lane 2) the second precipitation of purification containing the purified target protein (A1AT). Lane 3) protein marker.

(ii) Transformation of HFBII-intein-A1AT in *E. coli* (strain DH5α), similar to Example 2;

(iii) Transformation of *Pichia pastoris* and selection of *Pichia pastoris* transformants, similar to Example 3. In this case, DNA amplified by the PCR was found to be about 2 Kb in size for A1AT, as indicated by agarose gel electerophoresis (FIG. 3b);

(iv) Expression of recombinant chimeric protein HFBII-intein-A1AT, similar to Example 4 (FIG. 4). In this case, the measurement of expression by ELISA was performed using human serpin A1 Duoset ELISA kit (R & D systems, DY1268); and (v) Purification of A1AT protein as a target protein, similar to Example 5. The results of SDS-PAGE indicated that the A1AT was separated from the other components with a high purity (FIG. 6).

The results of ELISA experiments verified the presence of recombinant A1AT in the dissolved solution of the second precipitate and its absence in the solution of the first precipitate.

The activity of the produced recombinant A1AT in the cell culture supernatant and the first and second precipitations was measured by elastase inhibitory capacity (EIC) according to Tavasoli et al. (2017). The results of EIC indicated that recombinant A1AT was in active form in supernatant of cell culture. The presence of elastase inhibitory activity was detected in the second precipitation while no elastase inhibitory activity was seen in the first precipitation.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

REFERENCES

US Patent Documents

US 20150353597 A1 November 2015 Chen et al.
US 20150057434 A1 February 2015 Schelle et al.
US 20060141570 A1 June 2006 Wood et al.

OTHER PUBLICATIONS

Du J and Rehm B H A, "Purification of target proteins from intracellular inclusions mediated by intein cleavable polyhydroxyalkanoate synthase fusions", Microb Cell Fact, 16:2553-2560, (2017).

Guan D, et al., "Split intein mediated ultra-rapid purification of tagless protein (SIRP)", Biotechnol Bioeng, 110:2471-2481, (2013).

Joensuu J J, et al., "Hydrophobin fusion for high-level transient protein expression and purification in *Nicotiana benthamiana*", Plant Physiol, 15:622-623, (2010).

Linder M, et al., "The hydrophobins HFBI and HFBII from *Trichoderma reesei* showing efficient interactions with nonionic surfactants in aqueous two-phase systems", Biomacromolecules, 2:511-517, (2001).

Linder M B, et al., "Efficient purification of recombinant proteins using hydrophobins as tags in surfactant-based two-phase systems", Biochem, 43:11873-11882, (2004).

Shah N H and Muir T W, "Inteins: Nature's Gift to Protein Chemists", Chem Sci, 5:446-46, (2014).

Shemella B, et al., "Mechanism for intein C-terminal cleavage: a proposal from quantum mechanical calculations", Biophys J, 92 847-853, (2007).

Tavasoli T, et al., "Enhancement of Alpha 1-antitrypsin Production in *Pichia pastoris* by Designing and Optimizing Medium Using Elemental Analysis", Iran J Biotech, 15:224-231, (2017).

Terpe K, "Overview of tag protein fusions: from molecular and biochemical fundamentals to commercial systems", Appl Microbiol Biotechnol, 60:523-533, (2003).

Topilina N I and Mills K V, "Recent advances in vivo applications of intein-mediated protein splicing", Mob DNA 5: 5, (2014).

Walsh G, "Proteins: biochemistry and biotechnology", John Wiley & Sons, (2014).

Wood D W and Camarero J A, "Intein applications: from protein purification and labeling to metabolic control methods", J Biol Chem, 289:14512-14519, (2014).

Wood D W, et al., "Optimized single-step affinity purification with self-cleaving intein applied to human acidic fibroblast growth factor", Biotechnol Prog, 16: 1055-1063, (2000).

We claim:

1. A method of purifying a target protein, the method comprising:
   (a) preparing a cell culture supernatant comprising a fusion protein, wherein the fusion protein comprising:
     (i) a target protein domain;
     (ii) a self-cleaving intein;
     (iii) at least one hydrophobin protein domain, wherein the intein is located between the target protein domain and the hydrophobin domain;
   (b) adding a C1-C3 alcohol to the cell culture supernatant making a first alcohol solution;
   (c) stirring the first alcohol solution forming a first stirred solution;
   (d) centrifuging the first stirred solution forming a first precipitate and a first supernatant, wherein the first supernatant comprising the fusion protein;
   (e) separating the first supernatant comprising the fusion protein;
   (f) adding a C1-C3 alcohol to the first supernatant making the second alcohol solution;
   (g) stirring the second alcohol solution forming a second stirred solution;
   (h) centrifuging the second stirred solution forming a second supernatant and a second precipitate, wherein the second precipitate comprising the target protein; and
   (i) separating the second precipitate comprising the target protein to yield a substantial amount of the purified target protein,
   wherein the intein is Ssp DnaB mini-intein from *Synechocystis*,
   wherein the volume fraction of C1-C3 alcohol added in making the first alcohol solution in step (b) is from about 50% (v/v) to about 75% (v/v), and
   wherein the volume fraction of the C1-C3 alcohol added in making the second alcohol solution in step (f) is from about 50% (v/v) to about 66.66% (v/v).

2. The method of claim 1, wherein the cell culture supernatant is prepared comprising the steps:
   (i) constructing a plasmid expressing the fusion protein in a host cell;
   (ii) culturing the host cell transfected with the plasmid forming a recombinant cell culture medium, wherein the fusion protein is expressed in a plurality of the host cells;
   (iii) allowing the fusion protein to leave the host cells either by cell secretion or cell lysis into the recombinant cell culture medium;
   (iv) centrifuging the recombinant cell culture medium forming the cell culture supernatant comprising the fusion protein; and
   (v) separating the cell culture supernatant to be used for the purification of the target protein.

3. The method of claim 1, wherein the intein undergoes c-terminal cleavage as a result of a shift in pH and temperature.

4. The fusion protein of claim 1, wherein the intein comprises an additional Cystein amino acid at its C-terminal for improving splicing.

5. The fusion protein of claim 1, wherein the at least one hydrophobin domain is covalently attached to the intein by an amino acid linker.

6. The method of claim 1, wherein the target protein is vascular endothelial growth factor $A_{165}$.

7. The method of claim 1, wherein the target protein is human alpha 1-antitrypsin.

8. The method of claim 1, wherein the hydrophobin is hydrophobin number II from *Trichoderma reesei*.

9. The method of claim 1, wherein the first supernatant is separated from the first precipitate by decanting the first supernatant.

10. The method of claim 1, wherein the second precipitate is separated from the second supernatant by decanting the second supernatant.

11. The method of claim 1, wherein the volume fraction of C1-C3 alcohol added in making the first alcohol solution in step (b) is about 66.66% (v/v), and the alcohol is C2 alcohol.

12. The method of claim 1, wherein the volume fraction of the C1-C3 alcohol in making the second alcohol solution in step (f) is about 54.54 (v/v), and the alcohol is C2 alcohol.

13. The method of claim 2, wherein the host cell is a strain from *Pichia pastoris*.

14. The method of claim 2, wherein the cell culture supernatant is separated by decanting the cell culture supernatant.

* * * * *

SEQUENCE LISTING

```
<160> NUMBER OF SEQ ID NOS: 7

<210> SEQ ID NO 1
<211> LENGTH: 86
<212> TYPE: PRT
<213> ORGANISM: Trichoderma reesei

<400> SEQUENCE: 1

Met Gln Phe Phe Ala Val Ala Leu Phe Ala Thr Ser Ala Leu Ala Ala
1               5                   10                  15

Val Cys Pro Thr Gly Leu Phe Ser Asn Pro Leu Cys Cys Ala Thr Asn
            20                  25                  30

Val Leu Asp Leu Ile Gly Val Asp Cys Lys Thr Pro Thr Ile Ala Val
        35                  40                  45

Asp Thr Gly Ala Ile Phe Gln Ala His Cys Ala Ser Lys Gly Ser Lys
    50                  55                  60

Pro Leu Cys Cys Val Ala Pro Val Ala Asp Gln Ala Leu Leu Cys Gln
65                  70                  75                  80

Lys Ala Ile Gly Thr Phe
                85

<210> SEQ ID NO 2
<211> LENGTH: 156
<212> TYPE: PRT
<213> ORGANISM: Synechocystis sp. PCC6803

<400> SEQUENCE: 2

Gly Ala Ile Ser Gly Asp Ser Leu Ile Ser Leu Ala Ser Thr Gly Lys
1               5                   10                  15

Arg Val Ser Ile Lys Asp Leu Leu Asp Glu Lys Asp Phe Glu Ile Trp
            20                  25                  30

Ala Ile Asn Glu Gln Thr Met Lys Leu Glu Ser Ala Lys Val Ser Arg
        35                  40                  45

Val Phe Cys Thr Gly Lys Lys Leu Val Tyr Ile Leu Lys Thr Arg Leu
    50                  55                  60

Gly Arg Thr Ile Lys Ala Thr Ala Asn His Arg Phe Leu Thr Ile Asp
65                  70                  75                  80

Gly Trp Lys Arg Leu Asp Glu Leu Ser Leu Lys Glu His Ile Ala Leu
            85                  90                  95

Pro Arg Lys Leu Glu Ser Ser Ser Leu Gln Leu Ser Pro Glu Ile Glu
            100                 105                 110

Lys Leu Ser Gln Ser Asp Ile Tyr Trp Asp Ser Ile Val Ser Ile Thr
            115                 120                 125
```

```
Glu Thr Gly Val Glu Val Phe Asp Leu Thr Val Pro Gly Pro His
            130                 135                 140

Asn Phe Val Ala Asn Asp Ile Ile Val His Asn Cys
145                 150                 155

<210> SEQ ID NO 3
<211> LENGTH: 12
<212> TYPE: PRT
<213> ORGANISM: Artificial Sequence
<220> FEATURE:
<223> OTHER INFORMATION: An emprical peptide linker with 12 amino acids
      at the N-terminal.

<400> SEQUENCE: 3

Asn Asn Gly Asn Asn Gly Leu Glu Leu Arg Glu Ser
1               5                   10

<210> SEQ ID NO 4
<211> LENGTH: 165
<212> TYPE: PRT
<213> ORGANISM: Homo sapiens

<400> SEQUENCE: 4

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Arg Lys His Leu Phe
        115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Arg Cys
145                 150                 155                 160

Asp Lys Pro Arg Arg
                165

<210> SEQ ID NO 5
<211> LENGTH: 1278
<212> TYPE: DNA
<213> ORGANISM: Artificial Sequence
<220> FEATURE:
<223> OTHER INFORMATION: Chemically synthesized sequence encoding the
      fusion protein hydrophobin II+ linker+ Dnab intein+ human VEGF.

<400> SEQUENCE: 5
gaattcgaaa cgatgcagtt cttcgctgtt gctttgttcg ctacttctgc tttggctgct      60
gtttgtccaa ctggttttgt tctccaaccca ttgtgttgtg ctacaaacgt tttggacttg    120
atcggtgttg actgtaagac tccaactatc gctgttgaca ctggtgctat tttccaggct    180
cactgtgctt ctaagggttc caagcctttg tgttgtgttg ctccagttgc tgaccaggct    240
```

```
ttgttgtgtc aaaaggctat cggtactttc aacaacggaa acaacggttt ggagttgaga    300
gaatccggtg ctatctctgg tgactccttg atttctttgg cttccactgg taagagagtt    360
tccatcaagg acttgttgga cgagaaggac ttcgagatct gggctattaa cgagcagact    420
atgaagttgg aatccgctaa ggtttccaga gttttctgta ctggaaagaa gttggtttac    480
atcttgaaaa ctagattggg tagaactatc aaggctactg ctaaccacag attcttgact    540
atcgacggtt ggaagagatt ggacgagttg tccttgaaag agcacattgc tttgccaaga    600
aaattggagt cctcctcctt gcaattgtcc ccagagattg agaagttgtc ccagtctgac    660
atctactggg actccatcgt ttccattact gagactggtg ttgaagaggt tttcgacttg    720
actgttccag gtccacacaa cttcgttgct aacgacatca tcgttcacaa ctgtgctcca    780
atggctgaag gtggtggtca aaaccaccat gaggttgtta agttcatgga cgtttaccag    840
agatcctact gtcacccaat cgagactttg gttgacattt ccaagagta cccagacgag    900
atcgagtaca tcttcaagcc atcctgtgtt ccattgatga gatgtggtgg ttgttgtaac    960
gacgagggat tggagtgtgt tccaactgaa gagtccaaca tcactatgca gatcatgaga   1020
atcaagccac accagggaca cacatcggt gagatgtctt tcttgcagca caacaagtgt   1080
gagtgtagac caaagaagga cagagctaga caagagaacc catgtggtcc atgttccgag   1140
agaagaaagc acttgttcgt tcaggatcca cagacatgta agtgttcatg taagaacact   1200
gactccagat gtaaggctag acagttggaa ttgaacgaga gaacttgtag atgtgacaag   1260
cctagaagat aaggtgaa                                                 1278
```

<210> SEQ ID NO 6
<211> LENGTH: 394
<212> TYPE: PRT
<213> ORGANISM: Homo sapiens

<400> SEQUENCE: 6

```
Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
```

-continued

```
                180                 185                 190
Lys Trp Glu Arg Pro Phe Glu Val Lys Asp Thr Glu Glu Asp Phe
            195                 200                 205

His Val Asp Gln Val Thr Thr Val Lys Val Pro Met Met Lys Arg Leu
210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
            245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
            275                 280                 285

Pro Lys Leu Ser Ile Thr Gly Thr Tyr Asp Leu Lys Ser Val Leu Gly
            290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
            355                 360                 365

Pro Phe Val Phe Leu Met Ile Glu Gln Asn Thr Lys Ser Pro Leu Phe
            370                 375                 380

Met Gly Lys Val Val Asn Pro Thr Gln Lys
385                 390
```

<210> SEQ ID NO 7
<211> LENGTH: 1971
<212> TYPE: DNA
<213> ORGANISM: Artificial Sequence
<220> FEATURE:
<223> OTHER INFORMATION: Chemically synthesized sequence encoding the fusion protein hydrophobin II+ linker+ Dnab intein+ human A1AT.

<400> SEQUENCE: 7

```
gaattcgaaa cgatgcagtt cttcgctgtt gctttgttcg ctacttctgc tttggctgct      60
gtttgtccaa ctggtttgtt ctccaaccca ttgtgttgtg ctacaaacgt tttggacttg     120
atcggtgttg actgtaagac tccaactatc gctgttgaca ctggtgctat tttccaggct     180
cactgtgctt ctaagggttc aagcctttg tgttgtgttg ctccagttgc tgaccaggct      240
ttgttgtgtc aaaaggctat cggtactttc aacaacggta acaacggatt ggagttgaga     300
gaatccggtg ctatctctgg tgactccttg atttctttgg cttccactgg taagagagtt     360
tccatcaagg acttgttgga cgagaaggac ttcgagatct gggctattaa cgagcagact     420
atgaagttgg aatccgctaa ggtttccaga gttttctgta ctggaaagaa gttggtttac     480
atcttgaaaa ctagattggg tagaactatc aaggctactg ctaaccacag attcttgact     540
atcgacggtt ggaagagatt ggacgagttg tccttgaaag agcacattgc tttgccaaga     600
aaattggagt cctcctcctt gcaattgtcc ccagagattg agaagttgtc ccagtctgac     660
atctactggg actccatcgt ttccattact gagactggtg ttgaagaggt tttcgacttg     720
actgttccag tccacacaa cttcgttgct aacgacatca tcgttcacaa ctgtagagct     780
gaagatccac aaggtgacgc tgctcaaaag actgatactt ctcaccacga tcaggaccac     840
```

```
ccaacattca acaagatcac tccaaacttg gctgagttcg ctttctcatt gtacagacag      900
ttggctcacc agtccaactc cactaacatt ttcttctcac ctgtttccat tgctactgct      960
ttcgctatgt tgtctttggg tactaaggct gacactcacg acgagatttt ggagggtttg     1020
aacttcaact tgactgagat cccagaggct cagattcacg aaggattcca agagttgttg     1080
agaactttga accagccaga ctcccagttg cagttgacta ctggtaacgg tttgttcttg     1140
tccgagggat tgaagttggt tgacaagttc ttggaggacg ttaagaagtt gtaccactcc     1200
gaggctttca ctgttaactt cggtgacact gaagaggcta agaagcagat caacgactac     1260
gttgagaagg gtactcaggg taagatcgtt gacttggtta aggaattgga cagagacact     1320
gttttcgctt tggttaacta catcttcttc aagggaaagt gggaaagacc attcgaggtt     1380
aaggacactg aggaagagga tttccacgtt gaccaggtta ctactgttaa ggttccaatg     1440
atgaagagat tgggtatgtt caacatccag cactgtaaga aattgtcctc ttgggttttg     1500
ttgatgaagt acttgggtaa cgctacagct atcttcttct tgccagacga gggaaagttg     1560
cagcacttgg aaaacgaatt gactcacgac attatcacaa aattcttgga gaacgaggac     1620
agaagatccg cttccttgca cttgccaaag ttgtccatca ctggtactta cgacttgaag     1680
tccgttttgg gacagttggg tatcactaag gttttctcca acggtgctga cttgtccggt     1740
gttacagaag aagctccttt gaagttgtct aaggctgttc acaaggctgt tttgacaatc     1800
gacgaaaagg gtactgaagc tgctggtgct atgttcttgg aagctatccc aatgtccatc     1860
ccaccgagag ttaagttcaa caagcctttc gttttcttga tgatcgagca gaacactaag     1920
tcacctttgt tcatgggtaa ggttgttaac ccaactcaga agtaaggtac c              1971
```